United States Patent [19]

Schoebrechts et al.

[11] Patent Number: 5,955,638
[45] Date of Patent: Sep. 21, 1999

[54] PROCESS FOR PREPARATION OF 2-CHLORO-1-PROPENE

[75] Inventors: Jean-Paul Schoebrechts, Grez-Doiceau; Francine Janssens, Vilvoorde, both of Belgium

[73] Assignee: Solvay (Société Anonyme), Brussels, Belgium

[21] Appl. No.: 09/150,192

[22] Filed: Sep. 10, 1998

[30] Foreign Application Priority Data

Sep. 24, 1997 [FR] France .................................... 97 11976

[51] Int. Cl.$^6$ .................................................. C07C 17/04
[52] U.S. Cl. ........................... 570/232; 570/231; 570/233
[58] Field of Search ..................... 570/231, 232, 570/233

[56] References Cited

U.S. PATENT DOCUMENTS

| | | | |
|---|---|---|---|
| 3,110,740 | 11/1963 | Peer et al. | 570/231 |
| 3,420,902 | 1/1969 | Olson et al. | |
| 4,480,121 | 10/1984 | Klun et al. | |
| 4,554,391 | 11/1985 | Klun et al. | 570/231 |
| 4,704,485 | 11/1987 | Mitchell et al. | 570/231 |
| 4,754,087 | 6/1988 | Mulhauser | 570/231 |

FOREIGN PATENT DOCUMENTS

| | | |
|---|---|---|
| 701874 | 1/1968 | Belgium . |
| 0132544A1 | 2/1985 | European Pat. Off. . |
| 1505099 | 12/1966 | France . |
| 387325 | 1/1933 | United Kingdom ................... 570/232 |
| 908219 | 10/1962 | United Kingdom ................... 570/231 |
| 1140439 | 7/1967 | United Kingdom . |

OTHER PUBLICATIONS

Chemical Abstract, vol.116, No.5, Feb. 3, 1992: "Preparation of 2–halo–1–alkene by reaction of alkene derivative or 1–alkene with hydrogen halide"—Kawamura et al.

*Primary Examiner*—Alan Siegel
*Attorney, Agent, or Firm*—Venable; George H. Spencer; Ashley J. Wells

[57] ABSTRACT

2-Chloro-1-propene is prepared by catalytic hydrochlorination of methylacetylene and/or of propadiene in a liquid medium containing at least one catalyst chosen from compounds of the metals from group VIIIa and from the lanthanides, and at least one organic solvent capable of dissolving the catalyst.

10 Claims, No Drawings

PROCESS FOR PREPARATION OF 2-CHLORO-1-PROPENE

The present invention relates to a process for the preparation of 2-chloro-1-propene.

2-Chloro-1-propene is an intermediate in the synthesis of 1,1,1,3,3-pentachlorobutane, which is itself a precursor of the corresponding fluoro derivative known under the abbreviation HFC-365mfc, which is used as a solvent and as a swelling agent in the preparation of polymeric cellular foams.

It is known practice to form 2-chloro-1-propene from a mixture of compounds comprising, in particular, methylacetylene and propadiene, by hydrochlorination in the gaseous phase in the presence of a supported catalyst (patent FR 1,505,099, Japanese patent application JP 03/206,053). However, the stability of such hydrochlorination catalysts used in the gaseous phase is insufficient for easy industrial exploitation. The toxicity of some of the catalysts used and their harmful impact on the environment also represent considerable drawbacks.

U.S. Pat. No. 4,480,121 describes such a process, carried out in the presence of steam at high temperature. However, it is well known that in the presence of water, hydrogen chloride forms a particularly corrosive medium.

Consequently, the aim of the present invention is to provide an alternative process for the preparation of 2-chloro-1-propene starting with methylacetylene or propadiene, in which the 2-chloro-1-propene is obtained in excellent yield and which does not have the drawbacks of the prior processes.

The invention thus relates to a process for the preparation of 2-chloro-1-propene by reaction of methylacetylene and/or propadiene with hydrogen chloride in a liquid medium containing at least (a) a hydrochlorination catalyst which comprises at least one compound chosen from the compounds of the metals from group VIIIa and of the lanthanides; and (b) an organic solvent capable of dissolving the catalyst.

Advantageously, the process according to the invention takes place in the substantial absence of water.

A nitrile, an organophosphorus compound or an ammonium salt can be used in particular as a solvent capable of dissolving the catalyst.

Solvents which can be used in particular in the process according to the invention are aliphatic nitriles of general formula $CH_3-(CH_2)_n-CN$ in which n is an integer from 3 to 7; aliphatic dinitriles of general formula $NC(CH_2)_m-CN$ in which m is an integer from 3 to 6; aromatic nitrites such as benzonitrile and toluonitrile; triethyl phosphite, tributyl phosphite, triphenyl phosphite, tributyl phosphate; and, preferably, the ammonium salts corresponding to general formula

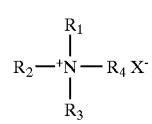

(I)

in which $R_1$, $R_2$, $R_3$ and $R_4$ represent hydrogen atoms, alkyl or aryl groups, which may be identical or different, at least one of them being an alkyl or aryl group and X represents an anion, preferably, the chloride anion. Optionally, $R_1$ and $R_3$ together can form, by means of the carbon atoms connecting them, a ring, for example a ring containing 5 or 6 carbon atoms, which can be substituted with alkyl groups. The term alkyl group is understood to refer to any linear or branched carbon-based chain, optionally substituted with one or more aryl groups. The term aryl group is understood to refer to any aromatic radical optionally substituted with one or more alkyl groups. The total number of carbon atoms in this amine compound is advantageously at least equal to 8. It is preferably at least equal to 12. The number of carbon atoms in this compound is generally not more than 40. It is preferably not more than 30.

The term ammonium salt is understood to denote one or more amine salts, including any mixture of salts of several amines, for example several isomeric compounds. Such a mixture of salts of several amines can also be used, in particular on account of its great availability or its lower cost than pure compounds. An example of such an ammonium salt comprising a mixture of various compounds corresponding to formula (I) is obtained by the reaction of hydrogen chloride with commercial products such as the primary tert-alkylamines Primene® 81-R and Primene® JM-T from Rohm & Haas Co., consisting of mixtures of $C_{12}-C_{14}$ and $C_{18}-C_{22}$ isomeric amines, respectively. In certain cases, it may also prove to be advantageous intentionally to mix chlorides of different amines on account of the existence of eutectics between these compounds, having a melting point below that of each of the constituents.

Particular preference is shown for ammonium salts which are liquid at room temperature. Most particular preference is shown for ammonium chlorides which are liquid at room temperature. In general, sterically hindered amines or those having at least two $C_6-C_{20}$ groups form chlorides that are liquid at room temperature.

Ammonium salts which are liquid at room temperature are those in which at least one of the four substituents on the nitrogen atom represents an alkyl group which has a long branched carbon-based chain and in which the number of carbon atoms in the compound is at least equal to 8, preferably at least equal to 12. Other ammonium salts which are liquid at room temperature are those in which at least two substituents on the nitrogen atom are $C_6-C_{20}$ alkyl groups.

Ammonium salts which can be used in the process according to the invention are, in particular, amine hydrochlorides, i.e. compounds of formula I in which $R_4$ represents hydrogen and X is a chloride ion. Methyltrioctylammonium chloride is another preferred ammonium salt.

The hydrochlorination catalyst used in the process of the present invention comprises at least one compound of a metal from group VIIIa or from the lanthanides (according to the 1970 IUPAC version of the Periodic Table of the Elements). Advantageously, the metal compounds used are chosen from the halides. Preference is shown for the chlorides or bromides, but any other compound capable of being converted into chloride in the presence of hydrogen chloride can also be used. The compounds of a metal from group VIIIa complexed with electron-rich systems such as amines, oxygen-containing compounds such as cyclic or acyclic ethers or carbonyl compounds, sulphur-containing compounds, aromatic compounds or compounds bearing aromatic rings can also be used. The salts formed between a metal from group VIIIa and an acidic organic compound, not only with carboxylic acids but also with other compounds, such as acetylacetone, are advantageously considered as metal compounds which can be used. Complexes of metals from group VIIIa in which the metal has the valency zero, such as the complexes formed with triphenylphosphine or triphenylphosphine oxide, can also be used as catalyst.

The compounds of the lanthanide metals which can be used in the present invention are generally chosen from cerium, praseodymium and neodymium compounds, or mixtures thereof. The cerium compounds are preferred. Cerium chloride is particularly preferred.

Preferably, the catalyst comprises at least one compound of a metal from group VIIIa. The compounds of metals from group VIIIa which can be used in the present invention are generally chosen from iron, cobalt, nickel, ruthenium, rhodium, palladium, osmium, iridium and platinum compounds, or mixtures thereof.

Advantageously, the compound of a metal from group VIIIa used is chosen from platinum, rhodium and palladium compounds. The platinum compounds are most particularly preferred.

Platinum compounds which can be used are a halide such as, for example, platinum(II) chloride, platinum(II) bromide and platinum(II) iodide or a platinochloride of an alkali metal or of an alkaline-earth metal, such as $Na_2PtCl_4$; hexachloroplatinic acid ($H_2PtCl_6$), $Na_2PtCl_6$, $K_2PtCl_6$, $(NH_4)_2PtCl_4$ or platinum(II) acetylacetonate may also be used. Platinum(II) acetylacetonate and platinum halides are preferred and, among the latter, platinum(II) chloride and platinum(II) bromide are particularly preferred.

Advantageously, the nature and/or the amount of catalyst used is such that all of the catalyst is in dissolved form in the organic solvent. However, it is also possible to use a catalyst in an amount or of a nature such that at least one fraction thereof is present in the liquid medium in dispersed solid form, without having a negative impact on the invention. The amount of catalyst used is generally greater than or equal to 1 millimole per liter of liquid medium. Preferably, it is greater than or equal to 10 millimol per liter of liquid medium. Advantageously, it is greater than or equal to 20 millimol per liter of liquid medium. The amount of catalyst is usually less than or equal to 200 millimole per liter of liquid medium. Preferably, it is less than or equal to 150 millimol per liter of liquid medium. Advantageously, it is less than or equal to 100 millimole per liter of liquid medium.

In a preferred embodiment of the process according to the invention, a co-catalyst is also used, which comprises at least one compound of at least one metal from groups Ib or IVb, such as copper, silver, tin or lead. A marked preference is shown for metals such as copper and tin, in particular copper. Preferably, the compound of a metal from groups Ib or IVb used as cocatalyst in this embodiment is a chloride. Particular preference is shown for copper(II) chloride, most particularly, when the catalyst is a platinum(II) halide. Generally, the co-catalyst is used in a molar ratio relative to the catalyst of greater than 0.1. Preferably, this molar ratio is greater than or equal to 1. Advantageously, this molar ratio is greater than or equal to 2. However, this molar ratio is usually less than 20. Preferably, this molar ratio is less than or equal to 15. Advantageously, this molar ratio is less than or equal to 10. The co-catalyst can be introduced at the start of the reaction, at the same time as the catalyst, or it can be introduced during the reaction.

Advantageously, besides the catalyst, the solvent and any co-catalyst, the liquid medium comprises at least one organic co-solvent. The choice of the nature of the organic co-solvent used is conditioned in particular by the need for it to be inert towards the reagents under the reaction conditions, for it to be miscible with the solvent at the reaction temperature and for it to be capable of dissolving it, in particular when this solvent is solid at room temperature. Moreover, for reasons of safety and ease of use, preference will be given to relatively non-volatile organic co-solvents. The choice of the organic co-solvent is also influenced by its capacity to dissolve methylacetylene and/or propadiene. Co-solvents which satisfy the various criteria outlined above are chosen from aliphatic, cycloaliphatic and aromatic hydrocarbons and mixtures thereof, for example $C_7$ to $C_{15}$ paraffins and alkylbenzenes, in particular xylenes, propylbenzenes, butylbenzenes and methylethylbenzenes. The co-solvent used is preferably chosen from commercial products consisting of mixtures of aliphatic hydrocarbons such as the product Isopar® from Esso or the product Shellsol® D70 from Shell, or mixtures of aromatic compounds such as the product Solvesso® from Esso or the product Shellsol® AB from Shell.

Co-solvents which have given good results are saturated aliphatic co-solvents such as the product Shellsol® D70, consisting of petroleum fractions having a boiling point of greater than or equal to about 190° C., and of less than or equal to about 250° C.

Other co-solvents which can be envisaged on the basis of the various criteria given above are certain heavy halogenated compounds, such as haloalkanes, halobenzenes and other halogenated derivatives of aromatic compounds.

It is often advantageous to use a solvent and a co-solvent, in particular when the liquid medium is too viscous to allow a perfect dispersion of the reagents in the solvent. In this case, the ratio by volume between the co-solvent and the solvent is generally greater than or equal to 0.01. Preferably, this ratio is greater than or equal to 0.10. Advantageously, this ratio is greater than or equal to 0.25. Generally, this ratio is less than or equal to about 100. Preferably, it is less than or equal to about 10. Advantageously, this ratio is less than or equal to 5.

In the process according to the invention, the liquid medium most particularly preferred contains platinum(II) bromide or platinum(II) chloride as catalyst, an ammonium chloride of formula (I), which is liquid at room temperature, as solvent, copper(II) chloride as co-catalyst and a mixture of saturated aliphatic hydrocarbons as co-solvent.

The process for the manufacture of 2-chloro-1-propene according to the invention is carried out by placing methylacetylene and/or propadiene in contact with hydrogen chloride in any suitable reactor containing the liquid medium. In the process according to the invention, it is preferred to use as reagent a mixture of hydrocarbons containing methylacetylene and propadiene, for example the mixture sold by Air Liquide under the name Tetrene®. Its molar composition is about 25% methylacetylene, 13% propadiene, 46% propylene, 4% propane and 12% $C_4$ hydrocarbons. Preferably, the liquid medium is saturated with hydrogen chloride before introducing the methylacetylene and/or the propadiene into the reactor.

The process according to the invention can be carried out conventionally, in a batchwise or continuous manner, in any apparatus which promotes gas-liquid exchange, such as a column with plates, a submerged column with stacks or a bubble column. Advantageously, the flow rate of the gases introduced into the reactor is adjusted so as to maximize the gas/liquid exchange surface.

In the process according to the invention, the molar ratio between the hydrogen chloride and the methylacetylene and/or the propadiene introduced into the reactor is generally greater than or equal to about 0.5. Preferably, this ratio is greater than or equal to 1. In general, this molar ratio is less than or equal to about 10. Preferably, this ratio is less than or equal to 5. Good results have been obtained with a molar ratio between the hydrogen chloride and the methylacetylene and/or the propadiene introduced into the reactor of less than or equal to about 2.5. The methylacetylene and/or the propadiene and the hydrogen chloride can be placed in contact in the reactor or can be mixed together prior to their introduction into the reactor.

The process of the invention can be carried out from room temperature up to about 200° C. At higher temperature, the catalyst has a tendency to degrade. The preferred reaction temperature, i.e. the one which offers the best compromise between production efficiency, yield and stability of the catalyst, is greater than or equal to 80° C. The best results are obtained at temperatures of greater than or equal to about 100° C. Preferably, the reaction temperature does not exceed about 180° C. A reaction temperature of less than or equal to about 160° C. is particularly preferred.

The pressure is generally greater than or equal to atmospheric pressure and less than or equal to 15 bar. Preferably, the pressure is less than or equal to 10 bar. Particular preference is shown for a pressure of less than or equal to 5 bar. Advantageously, the process of the invention takes place continuously at a pressure of 1 bar or at a pressure close to 1 bar. The flow rate of reagents, which are generally gaseous, must be sufficient to allow effective blending of the liquid medium, unless this medium is stirred mechanically.

In a continuous process, the residence time, which is the ratio between the volume of liquid medium in the reactor and the volumic flow rate of the reagents, is generally greater than or equal to 0.5 second. Advantageously, the residence time is greater than or equal to 1 second. In general, the residence time does not exceed 5 minutes. It is usually less than or equal to 2 minutes. Advantageously, it is less than or equal to 1 minute.

With the aim of increasing the amount of methylacetylene and/or of propadiene dissolved in the liquid medium, it is also possible, when the solvent used is an amine hydrochloride, to carry out the process according to the invention such that only the methylacetylene and/or the propadiene is introduced into the reactor in gaseous form, in which it reacts with the hydrogen chloride present in the liquid phase in the form of amine hydrochloride, this being regenerated by placing in contact a liquid shuttle which contains the amine with hydrogen chloride outside the reactor.

The invention is illustrated in the examples which follow.

EXAMPLE 1

The reaction was carried out in a Pyrex bubble column equipped with a jacket in which circulates oil thermostatically adjusted to the test temperature, and on which is mounted a cooled condenser for condensing the solvent and co-solvent vapours. 0.36 g of $PtCl_2$ was dissolved, with gentle heating, in a beaker in 15 ml of amine Primene 81R, sold by Rohm & Haas Co. 15 ml of the product Shellsol D70 were then added. When the platinum chloride was completely dissolved, the liquid phase was poured into the column preheated to 120° C. Hydrogen chloride was then injected at a flow rate of 6.25 ml per second for 30 minutes so as to convert the amine into the corresponding hydrochloride. Next, together with the hydrogen chloride, a mixture consisting, on a molar basis, of 25% methylacetylene, 13% propadiene, 46% propylene, 4% propane and 12% $C_4$ hydrocarbons was injected into the column at a flow rate of 6.25 ml per second. The concentration of catalyst in the liquid medium was 45 mmol/l.

The reaction products obtained over time were analysed by in-line gas-chromatographic analysis. The results are given in Table I below. In this table, the degree of conversion is the ratio between the initial concentration of methylacetylene and of propadiene minus its final concentration, divided by the initial concentration, multiplied by 100; the selectivity towards 2-chloro-1-propene is the ratio between the final concentration of 2-chloro-1-propene divided by the initial concentration of methylacetylene and of propadiene minus its final concentration, multiplied by 100; the yield of 2-chloro-1-propene is the ratio between the final concentration of 2-chloro-1-propene divided by the initial concentration of methylacetylene and of propadiene, multiplied by 100; the initial degree of conversion and the initial selectivity towards 2-chloro-1-propene given in Table 1, which are qualified, are the maximum values observed after placing the reactor under the established conditions for at least 10 hours. The stability of the catalytic system is the time required for the degree of conversion to fall by 10% relative to its maximum value obtained at the start of the test.

EXAMPLES 2–6

The test in Example 1 was repeated with other compounds from group VIIIa or from of the lanthanide group. The results are also given in Table I below.

TABLE I

| Example | Catalyst | Reaction temperature | Initial degree of conversion (%) | Initial selectivity towards 2-chloro-1-propene (%) | Stability (h) |
|---|---|---|---|---|---|
| 1 | $PtCl_2$ | 120° C. | 94 | 95 | 278 |
| 2 | $PtBr_2$ | 120° C. | 95 | 92 | 258 |
| 3 | Pt (II) acetylacetonate | 120° C. | 97 | 87 | 330 |
| 4 | $PtI_2$ | 120° C. | 94 | 87 | 238 |
| 5 | $H_2PtCl_6$ | 150° C. | 98 | 84 | 133 |
|   | $RhCl_3$ | 150° C. | 44 | 87 | not measured |

EXAMPLES 7–8

Examples 1 and 2 were repeated in the presence of $CuCl_2$ as co-catalyst, with a co-catalyst/catalyst molar ratio equal to 5. With the $PtCl_2$—$CuCl_2$ system, an initial degree of conversion of 97% and an initial selectivity towards 2-chloro-1-propene of 92% were obtained. The stability of the catalytic system as expressed above was 410 hours. With the $PtBr_2$—$CuCl_2$ system, an initial degree of conversion of 98% and an initial selectivity towards 2-chloro-1-propene of 90% were obtained. The stability of the catalytic system as defined above was 347 hours.

EXAMPLE 9

Example 1 was repeated using methyltrioctylammonium chloride as solvent. By carrying out the reaction at 140° C., an initial degree of conversion of 91% and an initial selectivity towards 2-chloro-1-propene of 93% were obtained. The stability of the catalytic system as defined above was 889 hours.

EXAMPLE 10

Example 1 was repeated using adiponitrile as solvent. By carrying out the reaction at 150° C., an initial degree of conversion of 40% and an initial selectivity towards 2-chloro-1-propene of 82% were obtained.

EXAMPLE 11

Example 1 was repeated using an equal-volume mixture of adiponitrile and of Primene 81 R as solvent, in the absence of co-solvent. By carrying out the reaction at 150° C., an initial degree of conversion of 82% and an initial selectivity towards 2-chloro-1-propene of 84% were obtained.

We claim:

1. A process for the preparation of 2-chloro-1-propene by reaction of methylacetylene and/or propadiene with hydrogen chloride in a liquid medium containing at least
   (a) a hydrochlorination catalyst which comprises at least one compound chosen from the compounds of the metals from group VIIIa and from the lanthanides; and
   (b) an organic solvent capable of dissolving the catalyst.

2. The process of claim 1, wherein the solvent is chosen from nitriles, organophosphorus compounds and ammonium salts, and mixtures thereof.

3. The process of claim 1, wherein the solvent is an ammonium salt of general formula

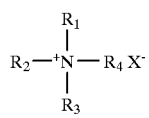

(I)

in which $R_1$, $R_2$, $R_3$ and $R_4$ represent hydrogen atoms, alkyl or aryl groups, which may be identical or different, at least one of them being an alkyl or aryl group and X represents an anion, preferably, the chloride anion.

4. The process of claim 3, wherein the number of carbon atoms in the ammonium salt is greater than or equal to 8 and less than or equal to 40.

5. The process of claim 1, wherein the compound of a metal from group VIII is a platinum, rhodium or palladium compound.

6. The process of claim 1, wherein the compound of a metal from group VIII is a platinum compound.

7. The process of claim 6, wherein the platinum compound is a platinum(II) halide.

8. The process of claim 1, wherein the co-catalyst comprising at least one compound of at least one metal from groups Ib or IVb is used.

9. The process of claim 1, wherein the liquid medium also comprises at least one organic co-solvent.

10. The process of claim 9, wherein the organic co-solvent is chosen from aliphatic, cycloaliphatic or aromatic hydrocarbons and mixtures thereof having a boiling point of greater than or equal to about 190° C. and of less than or equal to about 250° C.

* * * * *